United States Patent
Coldren

(10) Patent No.: US 6,767,515 B2
(45) Date of Patent: *Jul. 27, 2004

(54) TUNABLE LASER CAVITY SENSOR CHIP

(75) Inventor: Larry A. Coldren, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 405 days.

This patent is subject to a terminal disclaimer.

(21) Appl. No.: 09/886,360

(22) Filed: Jun. 20, 2001

(65) Prior Publication Data

US 2002/0018504 A1 Feb. 14, 2002

Related U.S. Application Data

(60) Provisional application No. 60/213,608, filed on Jun. 20, 2000.

(51) Int. Cl.[7] .............................................. G01N 30/02
(52) U.S. Cl. ......................... 422/156; 422/55; 422/56; 422/57; 422/68.1; 422/82.01; 422/82.02; 422/82.05; 422/82.06; 422/82.11
(58) Field of Search .......................... 422/56, 57, 68.1, 422/82.01, 82.02, 82.05, 82.06, 82.11

(56) References Cited

U.S. PATENT DOCUMENTS

| | | |
|---|---|---|
| 4,896,325 A | 1/1990 | Coldren |
| 5,637,458 A | 6/1997 | Frankel et al. |

FOREIGN PATENT DOCUMENTS

WO  PCT/EP99/00401  7/1999

OTHER PUBLICATIONS

Beregovski, Y. et al, "Design and Characteristics of DBR–laser–based environmental sensors", Sensors and Actuators B, Elsevier Sequoia S.A., Lausanne, CH, vol. 523, No. 1–2, Nov. 26, 1998, pp. 116–124, XP004151882.

Page 117, left–hand column, last paragraph—right–hand column, paragraph 2 p. 118, right–hand column, line 14—line 25 figure 1.

Hennig O, et al, "Distributed Bragg reflector laser–based sensor for chemical detection" Optics Communications, North–Holland Publishing Co. Amsterdam, NL, vol. 156, No. 4–6, Nov. 15, 1998 pp. 311–315, XP004143080.

Mason, B. et al. "Tunable Sampled–Grating DBR Lasers with Integrated Wavelength Monitors." *IEEE Photonics Technology Letters*, vol. 10, No. 8(Aug. 1998), pp. 1085–1087.

Mason, B. et al. "Ridge Waveguide Sampled Grating DBR Lasers with 22–nm Quasi–Continuous Tuning Range." *IEEE Photonics Technology Letters*, vol. 10, No. 9(Sep. 1998), pp. 1211–1213.

Meinhart, C.D. et al, "PIV measurements of a microchannel flow." Experiments in Fluids 27, (1999), pp. 414–419.

*Primary Examiner*—Jill Warden
*Assistant Examiner*—Sam P. Siefke
(74) *Attorney, Agent, or Firm*—Fulbright & Jaworski

(57) ABSTRACT

An integrated optical chip device for molecular diagnostics comprising a tunable laser cavity sensor chip using heterodyned detection at the juncture of a sensor laser and a reference laser, the sensor laser including exposed evanescent field material.

7 Claims, 4 Drawing Sheets

TUNABLE LASER CAVITY SENSOR CHIP

CROSS-REFERENCE TO RELATED APPLICATION

This application claims the benefit of United States Provisional Patent Application Ser. No. 60/213.608, filed Jun. 20, 2000

STATEMENT REGARDING FEDERALLY SPONSORED RESEARCH OR DEVELOPMENT

This invention was made with Government Support under Grant No. N00014-96-1-G014, awarded by the Office of Naval Research. The Government has certain rights in this invention.

FIELD OF THE INVENTION

This invention relates to laser sensors using heterodyned laser light.

BACKGROUND OF THE INVENTION

In recent years, lasers have been put to use in molecular diagnostics. Robert Frankel et al. U.S. Pat. No. 5,637,458 (the disclosure of which is incorporated herein by reference) describes a system for biomolecular separation and detection of a molecular species that uses a solid state laser detector formed with a sample channel. The presence of a molecular species is indicated by a frequency shift in the laser's output which is detected by optical heterodyning the laser's output with the output of a reference laser. The interior of the sample channel can, optionally, be coated with a ligand for binding a molecular species of interest. The system involves rather complex preprocessing of the sample by electro-osmotic separation in channels that are lithographically formed in a two dimensional planar substrate and/or by a nanostructural molecular sieve formed of spaced apart posts defining narrow channels. Although an at tempt at integrated system is provided by U.S. Pat. No. 5,637,458, it does not entirely provide a fully integrated optical chip device.

Also recently, highly coherent semiconductor lasers and laser arrays have been developed primarily for telecommunications applications. See for example C. E. Zah et al., IEEE Photon. Technol. Lett., vol. 8, pp 864–866, July, 1996. In addition, widely tunable semiconductor lasers have been developed, in particular, sampled-grating distributed Bagg reflector (SGDBR) lasers. See, for example "Tunable Sampled-Grading DBR Lasers with Integrated Wavelength Monitors," by B. Mason et al., *IEEE Photonics Technology Letters*, Vol. 10, No. 8 August 1998; 1085–1087 and "Ridge Waveguide Sampled Grating DBR Lasers with 22-nm Quasi-Continuous Tuning Range," by B. Mason et al., *IEEE Photonics Technology Letters*, Vol. 10, No. 9 September 1998, 1211–1213. These widely tunable lasers are based on the use of two multi-element mirrors as described in Coldren U.S. Pat. No. 4,896,325. The former also includes a Y-branch splitter with a detector in each branch for wavelength determination. Disclosures of the foregoing three publications and Coldren U.S. Pat. No. 4,896,325 are incorporated herein by reference.

SUMMARY OF THE INVENTION

The present invention provides an optical chip device usable for molecular diagnostics, what I call a tunable laser cavity sensor (TLCS). The TLCS is formed from a reference laser and a sensor laser, each comprising a waveguide having a gain section, a partially transmissive mirror section, and a coherent light beam output section, one or both of the waveguides having a phase control section. The light beam output sections of the reference and sensor lasers are joined to enable the coherent light from these sections to interfere, providing a heterodyned frequency. The sensor laser has a thinned waveguide region exposing evanescent field material to form a cavity and which detects the presence of a molecule by a heterodyned frequency shift.

DETAILED DESCRIPTION OF THE INVENTION

Figure 1:
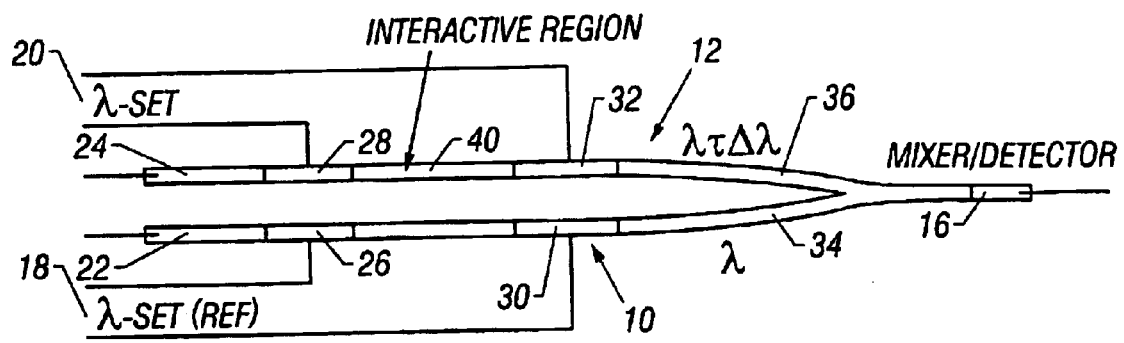
FIG. 1 is a top plan schematic view of a heterodyned tunable reference and sensor lasers with an intracavity sensor region.

The tunable laser cavity sensor (TLCS) optical sensor of this invention is shown in top plan view schematically in FIG. 1. Two distributed-bragg reflector (DBR) tunable lasers 10 and 12 are integrated with a Y-branch coupler 14 and a photodetector 16. One of the DBR tunable lasers 10 is a reference laser, the other 12 being a sensor laser. The photodetector 16 provides heterodyne detection of small changes in amplitude or frequency of the sensor laser 12 relative to the reference laser 10. As is known, the frequencies of the reference and sensor lasers can be set, as indicated at 18 and 20 by adjustment of the control sections, more particularly by adjustment of the respective gain 22, 24 and phase 26, 28 sections of the waveguides. Each waveguide has a partially transmissive grating mirror section 30 and 32 and a coherent light beam output section 34 and 36 which are joined at the mixer detector section 16.

In the illustrated embodiment, the interactive region 40 of the sensor waveguide is formed between the gain and phase control sections, respectively 24 and 28, and the sampled-grating mirror section 32. However, the particular order of the components between the mirrors is not critical and other configurations are equally useable. Thus all permutations of the locations of the gain section 24, phase control section 28 and interactive region 40 can be used. For example, the order from the cleaved facet 12 (FIG. 2) can be phase control section 32, gain section 28 and interactive region 40, etc. Also, while a phase control section is shown on both the reference laser 10 and sensor laser 12 it is sufficient to have it on only one of the lasers in order to tune one to the other.

As indicated, the left ends of the lasers 10 and 12 are formed by cleaved facets. As described below, both the left-end facet mirrors and the right-side grating mirrors can be sampled-grating mirrors to provide for wider tunability of the lasers output wavelength, in which case, the opposed sampled-grating mirrors would preferably have different sampling periods. Using lasers with different sampled grating periods is described in the aforementioned Coldren U.S. Pat. No. 4,896,325.

As shown, the frequency output of the sensor waveguide differs by $\pm\Delta\lambda$ from the frequency of their reference waveguide. By adjusting the tuning electrodes as shown in FIG. 1, one can enhance the measurement resolution by tuning to possible molecular bond resonances, e.g. in the 1550 nm wavelength range. Researchers at the University of California in Santa Barbara have pioneered DBR lasers with extended tuning ranges-so called sampled-grating-DBR lasers. The lasing wavelengths of these lasers can be tuned up to 100 nm, enabling the measurement of the index of the perturbing species versus wavelength over a relatively wide range to better identify their chemical nature.

Figure 2:
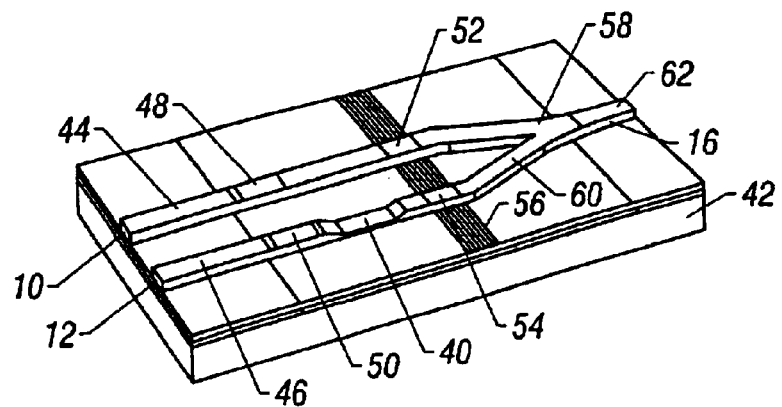
FIG. 2 is a bottom perspective view showing the tunable laser cavity sensor with control electrodes for gain, phase, and mirror currents.

Referring to FIG. 2, the TLCS is shown in more detail. The tunable cavity sensor is fabricated by integrating a tunable DBR sensor laser 10 with a reference laser 12 and combining them into a heterodyning detector 16 to accurately monitor changes in the modal index or loss due to adsorbates or interactions at the surface of a thinned interaction region 40 on the sensor laser 10. The InP chip 42 is formed with reference and sensor lasers 10 and 12, as will be described in more detail hereinafter, each of which carries gain control electrodes, respectively, 44, 46 and phase control electrodes, respectively, 54, 56 spaced from mirror control electrodes, respectively, 48, 50 overlying a partially transmissive grating mirror 56.

Figure 8:
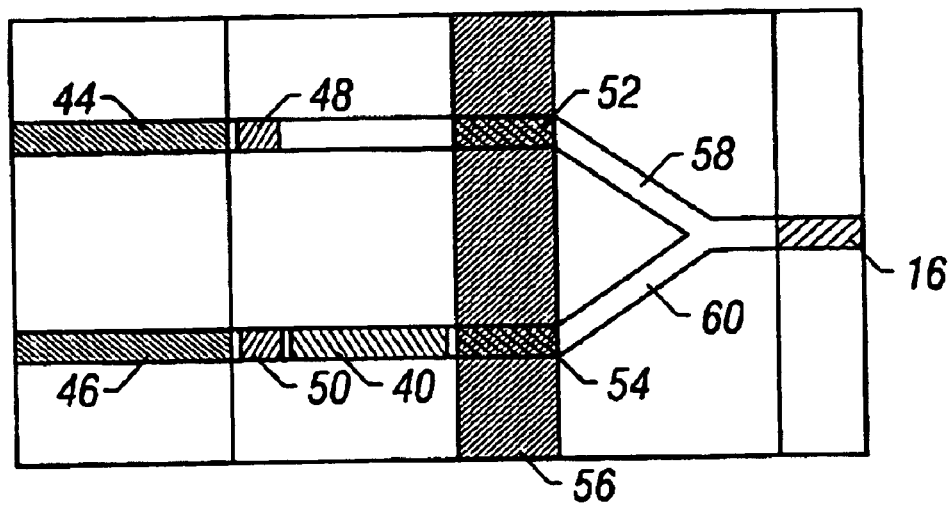
FIG. 8 is a schematic plan view of the tunable laser cavity sensor of FIG. 2.
Figure 9:
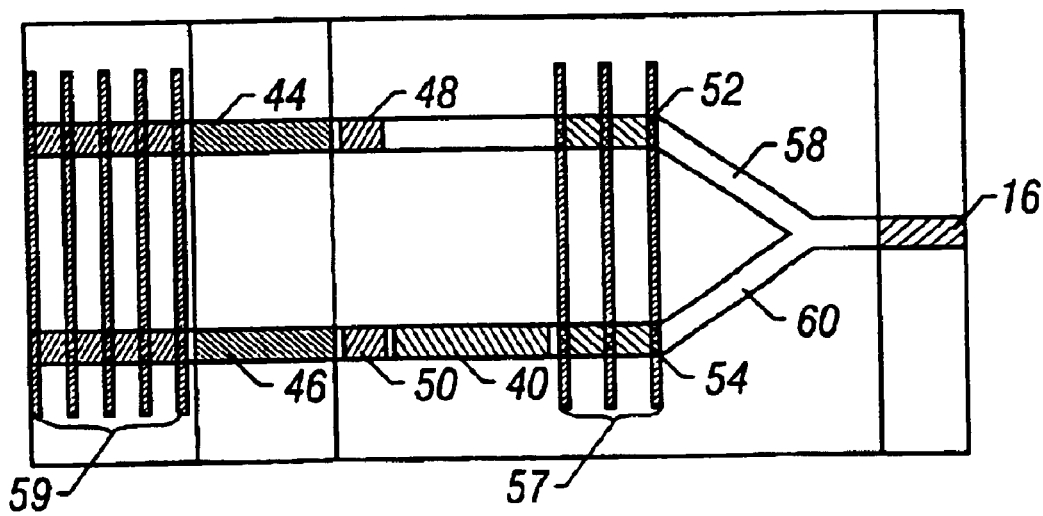
FIG. 9 is a schematic plan view of t tunable laser cavity sensor similar to that of FIG. 8, but with left and right side sampled-grating mirrors.

FIGS. 8 and 9 show schematic plan views of TLCSs using either a simple DBR partially transmissive mirror or two SGDBRs, respectively. The TLCS of FIG. 8 is that of FIG. 2 shown in plan view, with corresponding lead lines. In the TLCS of FIG. 9, the SGDBR configuration replaces the simple grating on the right side as well as the opposite laser facet mirror with sampled-grating mirrors, respectively 57 and 59, for extended tuning range.

As described with respect to FIG. 1, the reference and sensor coherent light beam output sections 52 and 65 join to deliver interfering light beams at the detector 16, sensed at a detector electrode 62 thereon. Although a "Y-branch" waveguide combiner element 58 & 60 is shown, another type of waveguide combiner, such as a "Multimode-interference" element may also be employed as is well known to those skilled in the art. The cladding of the sensor laser waveguide 12 is thinned to form the sensor cavity 40 to expose the evanescent fields of the lasing mode, and provide an interaction region. As in Frankel et al., U.S. Pat. No. 5,637,458, the surface of the cavity 40 can be coated with any of various ligands for binding the molecular species of interest, wherein a particular reaction occurs on the surface, or an antigen binds to an antibody adsorbate on the surface, a change in index of refraction, $\Delta n_s$, will occur at the region just above the surface. Since a portion of the laser mode, $\Gamma_{xy}$, fills this transverse region, the modal index is changed by an amount, $\Gamma_{xy}\Delta n_s$. Also, the interaction region extends along the axis of the laser to fill an axial fraction $\Gamma_z$, of the cavity, so that the net fill-factor for region in which the perturbation takes place is $\Gamma_{xy}\Gamma_z$.

Since the lasing wavelength changes in direct proportion to the net weighted change in index (and frequency as the direct negative), the relative change in laser output wavelength, $\lambda$, (or frequency, f) is given by:

$$\frac{\Delta\lambda}{\lambda} = \Gamma_{xy}\Gamma_z\frac{\Delta n_s}{n} = -\frac{\Delta f}{f}$$

For a typical sensing configuration, $\Delta n_s=0.1$, and $\Gamma_{xy}\Gamma_z=0.01$, and assuming the average index of the laser cavity is n=3.3, then $\Delta\lambda=0.05$ nm, or $\Delta f=-6$ GHz@$\lambda=1550$ nm. Now, if this deviation were to be measured in the optical domain, a quarter-meter or larger spectrometer would be necessary to obtain sufficient resolution to see the effect, which would be very difficult at the chip level. However, with the heterodyne detector of the TLCS of this invention, the shifted optical frequency can be down converted to the VHF radio frequency range where simple frequency counters can be used to measure the difference frequency with 1 Hz accuracy. Using heterodyne detection with two semiconductor lasers, a 6 GHz frequency shift can be measured with an accuracy of about 10 MHz, because this is the approximate linewidth of such lasers.

Put another way, again assuming the index shift in the small perturbation region, $\Delta n_s=0.1$, the net fill-factor of this region relative to the volume of the guided mode can be as small as $\Gamma_{xy}\Gamma_z=(10\text{ MHz})(3.3)/(0.1)(193\text{ THz})=1.7\times10^6$ Then, for example, if the transverse over lap, $\Gamma_{xy}$, is only 0.1% (very conservative estimate of the evanescent field), the axial $\Gamma_z$, can be as small as 0.17%. Therefore, with a net laser cavity length of 500 $\mu$m, single submicron particles can be detected.

The relative frequency change, $\Delta f/\Delta f$, of the laser is just equal to the relative modal index change times a fill factor, $\Gamma\Delta n/n$, and this frequency change, $\Delta f$, can be measured very accurately in the radio frequency (RF) range after down conversion by mixing with the unperturbed laser in the heterodyne detector, to measure changes in modal index of refraction inside the sensor laser cavity 48 with a resolution estimated at, $\Delta f/f=10$ MHz/200 THz$\approx 10^{-7}$.

In many situations it may be desired to detect more than one kind of molecular species. This may be possible by sweeping the wavelengths of the reference and sensor lasers by applying suitable currents to the control electrodes and observing characteristic resonances in the index measurement vs. $\lambda$. The use of a widely-tunable laser such as a sampled-grating DBR will facilitate this option.

Figure 3:
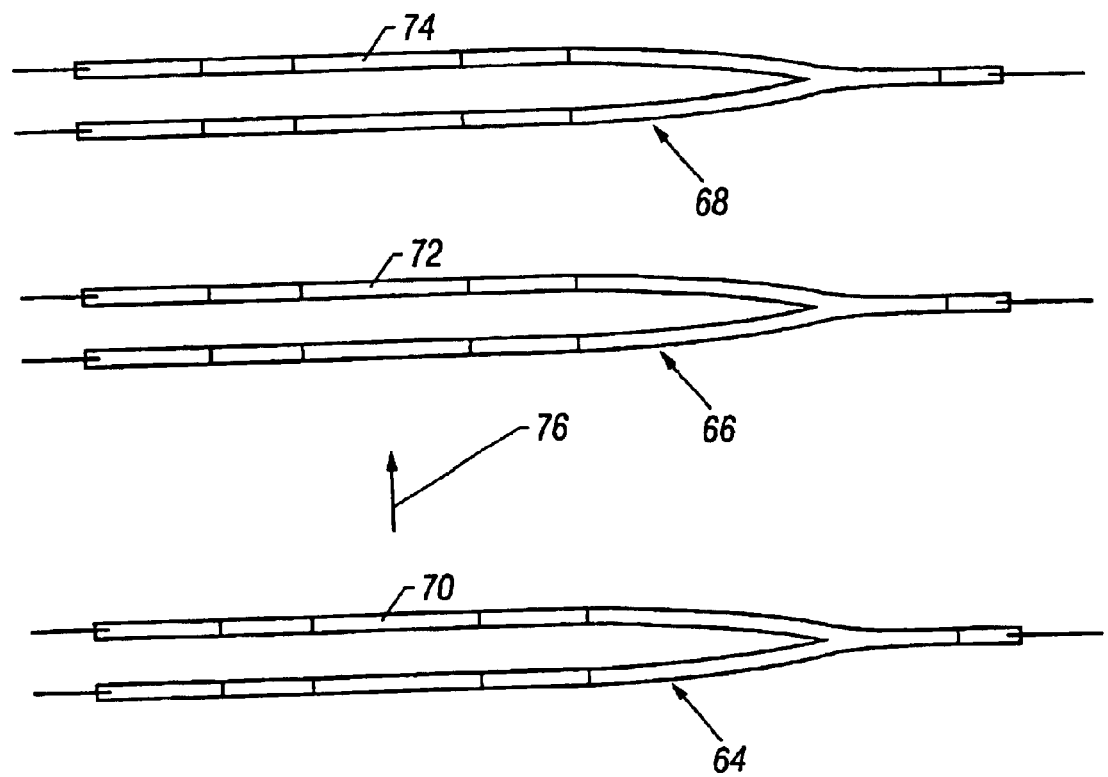
FIG. 3 is a top plan schematic view of a one-dimensional tunable laser cavity sensor array composed of multiple heterodyne tunable lasers with intracavity interaction regions.

Another approach to detect a multiplicity of species is to use one-dimensional TLCS array on the same chip, as illustrated in FIG. 3. A plurality of TLCSs which can be a dozen or more, but of which only three TLCSs 64, 66 and 68 are shown. The TLCSs form an array with successive interactive regions 70, 72 and 74, whereby fluid flows serially from the first interactive region 98 to the last interactive region 74, as shown by the arrow 76.

Each sensor cavity could measure a different molecular species. The practical number of TLCS array elements and thus sensed molecular species, is mainly limited by the desired to finite chip size. The active elements, including the two DBR lasers are spaced, e.g., by about 500 $\mu$m so as to allow space for contacts and to avoid cross talk. Again, spectral index information can also supplement the index information at each element if the wavelengths are varied across some range.

In fabricating the TLCS chip, known InP growth and fabrication procedures and DBR laser fabrication characterization procedures can be used. Existing 3-D beam propagation modeling (BPM) software can be utilized to provide inclusion of lateral and transverse variations in straight guides, such as in the interaction region, as well as the actual variations in bends, such as in the Y-branches, offset regions for gain, and detector circuitry, as shown in FIG. 2, will be used.

Figure 4:
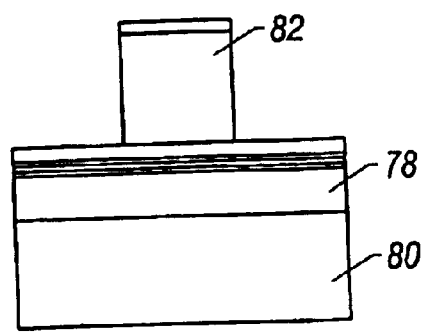
FIG. 4 is a cross-sectional, schematic view of a ridge waveguide usable in the present invention.
Figure 5:
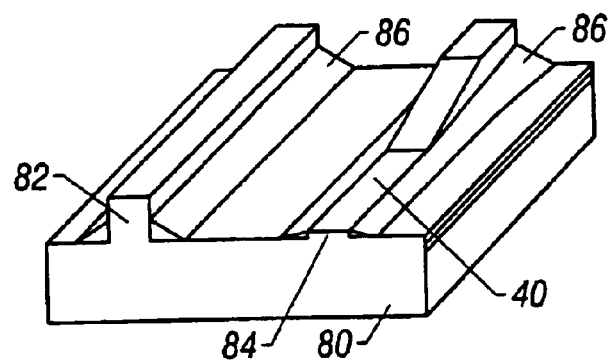
FIG. 5 is a cross sectional perspective view of reference and sensor ridge waveguides.

Referring to FIGS. 4 and 5, after a first growth, the lower band gap gain/detector layers are removed in the passive sections and the grating lines are etched into the underlying passive guide in the grating mirror section. In FIG. 4, a transverse cross section of a ridge waveguide is shown. The InGaAsP waveguide 78 is formed on an n-InP buffer and substrate 80. A p-InP ridge waveguide 82 is formed on the InGaAsP waveguide (regrowth) to provide the top cladding and contact layers, the latter formed by InGaAs. Sampled-grating lasers can be made with the same procedure. See, for example, Mason et al. (1998).

Referring to FIG. 5, to form the sensor cavity 48 containing the interaction region, the cladding over the optical waveguide is thinned to expose the vertical evanescent optical field. This results in a much smaller ridge height over the center of the guide but some lateral ridge structure must remain to provide lateral waveguiding. The resultant TLCS with its reference waveguide 82 and sensor waveguide 84 are thus formed. Inert polymer 86 is left at the corners of the ridge guides 82 and 84 to eliminate interactions with the fluid, which is especially important for the reference laser which is not to be affected by the fluid.

Figure 6:
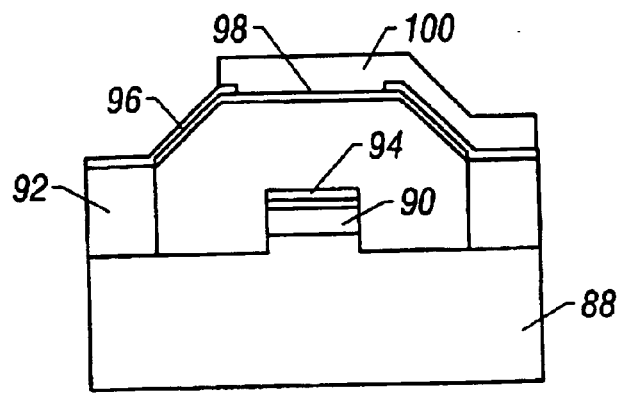
FIG. 6 is a cross sectional schematic view of a buried rib waveguide usable in the present invention.
Figure 7:
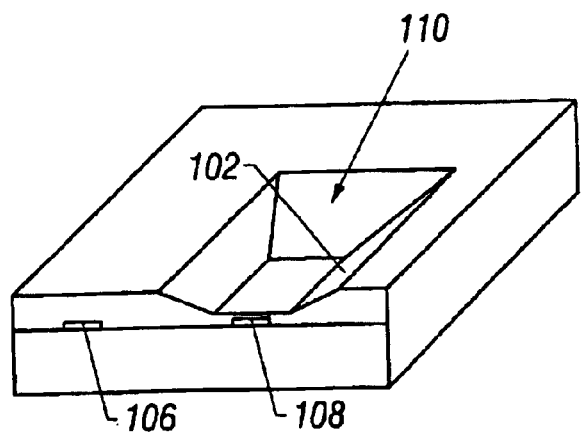
FIG. 7 is a cross sectional perspective schematic view of reference and sensor buried-rib waveguides.

Referring to FIGS. 6 and 7, in another embodiment of the invention, the waveguides can be buried-rib waveguides formed by etching away all the layers outside of the desired optical channel. As shown in FIG. 6, the n-InP substrate 99 carries a waveguide 90 and adjacent quantum well 94 in a p-InP layer contained in an implanted region 92 under a SiNx layer 96, an InGaAs contact layer 198 and Ti/Pt/Au contact layer 100 providing electrical contact.

As shown in FIG. 7, for the buried-rib embodiment, thinning results in a uniform lateral surface 102, obtained by removing the passive waveguide layer beneath the surface. The result is a TLCS 104 containing reference and sensor waveguides 106 and 108 with the sensor cavity 110 defining the interactive region of the TLCS.

While the invention has been described in terms of specific embodiments, various modifications can be made without departing from the scope of the invention.

What is claimed is:

1. A tunable laser cavity sensor chip comprising:
   (a) a reference laser and a sensor laser, each comprising a waveguide having a gain section, opposing mirrors including a partially transmissive mirror, and a coherent light beam output section, at least one of the waveguides having a phase control section, the coherent light beam output sections being joined to enable coherent light outputs of the reference and sensor lasers to interfere;
   (b) a sensor region physically separate from said phase control section formed through and exposing the evanescent optical field of the sensor laser, for receiving a sample to be diagnosed; and
   (c) a heterodyne detector at the juncture of the reference and sensor coherent light output sections for detecting a change in the frequency of the coherent light output from the sensor laser resulting from a change in the index of refraction of fluid in the sensorcavity.

2. The chip device of claim 1 wherein the mirror on each laser opposing the partially transmissive mirror is a facet mirror.

3. The chip device of claim 1 wherein the partially transmissive mirror and the opposing mirror are both sampled-grating mirrors having different sampling periods.

4. The chip device of claim 1 in which said exposed evanescent field region is between the gain section and one of the mirrors of the sensor laser.

5. The chip device of claim 1 in which the sensor laser includes said phase control section.

6. A system for the identification of a plurality of molecular species comprising a plurality of pairs of reference and sensor lasers of claim 1 having a common source of molecules to be diagnosed.

7. The system of claim 6 in which the outlet of one pair of reference and sensor lasers is connected in series to the outlet of another pair of reference and sensor lasers.

* * * * *